(12) United States Patent
Lehmann

(10) Patent No.: US 9,151,708 B2
(45) Date of Patent: Oct. 6, 2015

(54) ADAPTABLE CELL DESIGN FOR A SPECTROSCOPY APPARATUS

(75) Inventor: Kevin K. Lehmann, Crozet, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 14/006,818

(22) PCT Filed: Mar. 23, 2012

(86) PCT No.: PCT/US2012/030395
§ 371 (c)(1),
(2), (4) Date: Dec. 17, 2013

(87) PCT Pub. No.: WO2012/135044
PCT Pub. Date: Oct. 4, 2012

(65) Prior Publication Data
US 2014/0110599 A1    Apr. 24, 2014

Related U.S. Application Data

(60) Provisional application No. 61/569,527, filed on Dec. 12, 2011, provisional application No. 61/467,467, filed on Mar. 25, 2011.

(51) Int. Cl.
*G01N 21/03* (2006.01)
*G01J 3/42* (2006.01)
*G01N 21/39* (2006.01)

(52) U.S. Cl.
CPC .............. *G01N 21/0303* (2013.01); *G01J 3/42* (2013.01); *G01N 2021/0364* (2013.01); *G01N 2021/391* (2013.01)

(58) Field of Classification Search
USPC ..................... 250/428, 339.07, 340
See application file for complete search history.

(56) References Cited

U.S. PATENT DOCUMENTS

| | | | |
|---|---|---|---|
| 4,291,988 A | 9/1981 | Dixon, Jr. et al. | |
| 5,544,186 A | 8/1996 | Sauer et al. | |
| 6,241,397 B1 * | 6/2001 | Bao et al. | 385/73 |
| 7,012,696 B2 | 3/2006 | Orr et al. | |
| 7,063,466 B2 * | 6/2006 | Ferguson | 385/78 |

(Continued)

FOREIGN PATENT DOCUMENTS

| | | |
|---|---|---|
| JP | 04-208584 A | 7/1992 |
| JP | 07-270308 A | 10/1995 |

(Continued)

OTHER PUBLICATIONS

"European Application Serial No. 12762971.5, Extended European Search Report mailed Oct. 16, 2014", 14 pgs.

(Continued)

*Primary Examiner* — Phillip A Johnston
*Assistant Examiner* — Hsien Tsai
(74) *Attorney, Agent, or Firm* — Schwegman Lundberg & Woessner, P.A.

(57) ABSTRACT

An adjustable optical cell assembly includes a hollow body defining a cavity and a plurality of optical elements rigidly affixed within the cavity. A first actuator is configured to apply a force to an external surface of the hollow body sufficient to elastically deform at least a portion of the hollow body such one of a distance and a relative orientation between first and second optical elements of the plurality of optical elements is responsively altered.

17 Claims, 3 Drawing Sheets

(56) References Cited

U.S. PATENT DOCUMENTS

| | | | |
|---|---|---|---|
| 2003/0021306 A1* | 1/2003 | Fernald et al. | 372/20 |
| 2005/0052653 A1* | 3/2005 | Fidric | 356/437 |
| 2006/0203237 A1* | 9/2006 | Ji et al. | 356/246 |
| 2010/0012843 A1* | 1/2010 | Miller | 250/339.07 |

FOREIGN PATENT DOCUMENTS

| | | |
|---|---|---|
| JP | 08-043306 A | 2/1996 |
| JP | 10-326926 A | 12/1998 |
| JP | 11-094738 A | 4/1999 |
| WO | WO-2012/135044 A1 | 10/2012 |

OTHER PUBLICATIONS

"European Application Serial No. 12762971.5, Office Action mailed Nov. 4, 2013", 2 pgs.

"European Application Serial No. 12762971.5, Office Action mailed Nov. 4, 2014", 1 pg.

"International Application Serial No. PCT/US2012/030395, International Preliminary Report on Patentability mailed Oct. 10, 2013", 7 pgs.

"International Application Serial No. PCT/US2012/030395, International Search Report mailed Jul. 6, 2012", 2 pgs.

"International Application Serial No. PCT/US2012/030395, Written Opinion mailed Jul. 6, 2012", 6 pgs.

"Japanese Application Serial No. 2014-502648, Office Action mailed Dec. 2, 2014", (w/ English Translation), 8 pgs.

Gregory, Engel S, "Innovations in Cavity Enhanced Laser Absorption Spectroscopy: Using in situ Measurements to Probe the Mechanisms Driving Climate Change", *Proceedings NASA Earth Science Technology Conference*, (2003), 1-8.

Livio, Giafrani, "Cavity-enhanced absorption spectroscopy of molecular oxygen", *Journal of the Optical Society of America B*, 16, (12), (Dec. 1999), 2247-2254.

Tang, Yongxin, et al., "A rigid, monolithic but still scannable cavity ring-down spectroscopy cell", *Review of Scientific Instruments*, 83(4), (2012), 1-7.

"Korean Application Serial No. 10-2013-7027999, Office Action mailed May. 29, 2015", w/ English Claims, 10 pgs.

\* cited by examiner

ADAPTABLE CELL DESIGN FOR A SPECTROSCOPY APPARATUS

RELATED APPLICATIONS

This application claims priority from provisional application Ser. No. 61/467,467 filed on Mar. 25, 2011 in the name of Kevin K. Lehmann, assigned to the same assignee of the present application, and entitled CELL DESIGN FOR CAVITY RING-DOWN AND OTHER FORMS OF CAVITY ENHANCED SPECTROSCOPY AND RELATED METHOD THEREOF. This application also claims priority from provisional application Ser. No. 61/569,527 filed on Dec. 12, 2011 in the name of Kevin K. Lehmann, assigned to the same assignee of the present application, and entitled CELL DESIGN FOR CAVITY RING-DOWN AND OTHER FORMS OF CAVITY ENHANCED SPECTROSCOPY AND RELATED METHOD THEREOF. Each of these applications is hereby fully incorporated herein by reference.

TECHNICAL FIELD

The present invention relates generally to the field of spectroscopy, and more particularly to systems and methods for an adaptable cell design for a spectroscopy apparatus.

BACKGROUND OF THE INVENTION

Optical absorption is a method by which a composition of a sample can be determined, including both its chemical components and their respective concentrations. This finds application in a range of situations, including chemical process control, monitoring and control of impurities in manufacturing, monitoring compliance with emission regulations, monitoring the dispersal and chemical fate of natural and anthropomorphic species, combustion diagnostics, medical diagnostics, and biomedical research.

SUMMARY OF THE INVENTION

In accordance with an aspect of the present invention, an adjustable optical cell assembly is provided. The assembly includes a hollow body defining a cavity and a plurality of optical elements rigidly affixed within the cavity. A first actuator is configured to apply a force to an external surface of the hollow body sufficient to elastically deform at least a portion of the hollow body such one of a distance and a relative orientation between first and second optical elements of the plurality of optical elements is responsively altered.

In accordance with another aspect of the present invention, an assembly includes an optical cell apparatus. The optical cell apparatus includes a hollow tubular body comprising a wall of the optical cell apparatus. The tubular body has longitudinally spaced first and second body ends and surrounds a longitudinal axis of the optical cell to define a member lumen therethrough. A first end member is substantially rigid and attached to the first body end to define a first optical cell end. A first optical element is located within the member lumen and fixedly attached to the first end member. A second end member is substantially rigid and attached to the second body end to define a second optical cell end. A second optical element is located within the optical cell and fixedly attached to the second end member. A first actuator is mounted external to the member lumen and configured to apply a force to an external surface of the optical cell apparatus in a direction substantially parallel to the longitudinal axis that is sufficient to elastically deform at least a portion of the optical cell apparatus such that a longitudinal distance between the first optical element and the second optical element is responsively altered.

In accordance with yet another aspect of the present invention, a method is provided for detecting the concentration of an analyte. An optical cavity, comprising a rigid body and first and second optical elements affixed to the rigid body, is excited with a laser producing light of a substantially fixed wavelength. The rigid body is elastically deformed in at least a first location to bring the laser and the cavity into resonance. Light emitted from the cavity is detected. The detected light is evaluated to determine the concentration of the analyte.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Cavity enhanced spectroscopy covers several related spectroscopic techniques that use low loss optical cavities to allow for detection of weak absorption of samples, principally gaseous samples. In order to use these techniques in portable instruments or instruments in environments subject to acceleration or vibration, a cell design is provided that maintains rigid alignment of the mirrors or prisms that make up the optical cavity. To inject a significant amount of light into such a cavity from a narrow bandwidth laser, it is necessary to bring the laser and cavity into resonance. Rather than modulating the wavelength of the excitation laser, which introduces uncertainty in the detection wavelength and decreases the accuracy of the measurement, an adjustable cell is provided that allows for tuning of the length of a rigid cell to achieve resonance. It can be applied to optical cavities formed from two or more high reflectivity mirrors or prisms.

The cell is monolithic and maintains a rigid alignment of any optical elements within the cavity. One or more high-resolution and high-force transducers are used to sweep the length of the cell by elastic deformation of the body of the cell. The cavity length is scanned more than one-half wavelength of the light used to excite the cavity, which ensures that at least one $TEM_{00}$ mode of the cavity will pass through resonance with the laser. One advantage of this cell is its use in a frequency-locked-laser cw-CRDS technique, which increases the frequency precision of the measurements compared to the alternative of sweeping the frequency of the laser along the free spectral range (FSR) of the cavity. It will be appreciated, however, that the cell can be used in any application in which a highly rigid but stable optical etalon is desirable.

Figure 1:
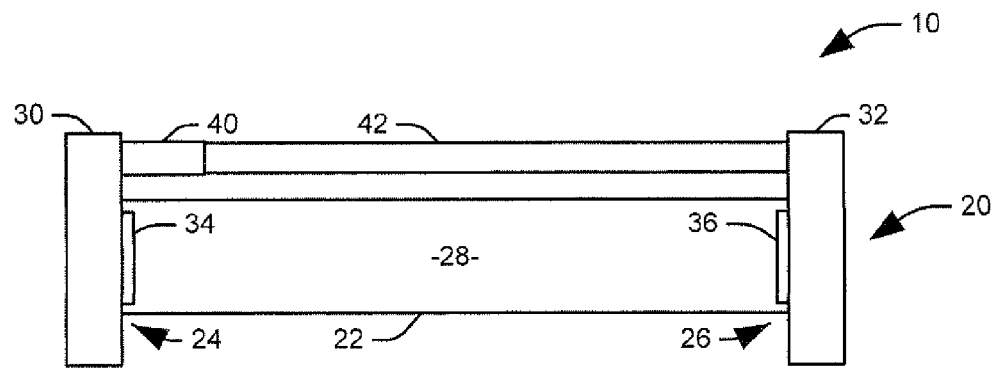
FIG. 1 is a cross-sectional view along a longitudinal axis of an assembly for providing an adjustable length optical cell apparatus in accordance with an aspect of the present invention.

FIG. 1 is a cross-sectional view along a longitudinal axis of an assembly 10 for providing an adjustable length optical cell apparatus 20 in accordance with an aspect of the present invention. The optical cell apparatus 20 includes a hollow tubular body 22 that forms a wall of the optical cell apparatus. The tubular body 22 has longitudinally spaced first and second body ends 24 and 26 and surrounds a longitudinal axis of an optical cell to define a member lumen 28 therethrough. In one implementation, the tubular body 22 can be a solid cylindrical tube formed from a rigid metal having an elastic limit sufficient to tolerate expansion on the order of several wavelengths of an associated light source (not shown). For example, the tubular body 22 can be formed from stainless steel or Invar.

First and second end members 30 and 32 are attached, respectively, to the first and second body ends 24 and 26 to define respective first and second optical cell ends. The first and second end members 30 and 32 are substantially rigid, and in combination with the tubular body 22, form a substantially airtight cavity for the optical cell assembly. It will be appreciated that each of the first and second end members 30 and 32 can be integral with the tubular body 22 or a separate article attached via a suitable method to form a durable, substantially airtight seal. In one implementation, the first end member 30 can comprise a vacuum flange, such as a Conflat flange.

First and second optical elements 34 and 36 are located within the member lumen and fixedly attached, respectively, to the first and second end members 30 and 32. The optical elements 34 and 36 can include one or more of mirrors, beam splitters, prisms, lens, or any other component for altering the direction, polarization, and coherence of a beam of light. In one implementation, each optical element 34 and 36 is a mirror having at least one surface formed from or coated with a material that is highly reflective at a frequency associated with the light source. In one implementation, the mirrors can be concave and positioned in a near confocal arrangement. To allow the optical elements 34 and 36 to maintain their alignment even when subjected to acceleration or vibration, they can be compressed against a surface of their respective end members 30 and 32.

In accordance with one aspect of the present invention, it has been determined that the optical cell apparatus 20, despite its rigidity, be sufficiently elastic that it is possible to stretch the optical cell apparatus 22 by a sufficient amount to alter the distance between the optical elements 34 and 36 by a distance of at least one half of the wavelength of the light used for detection, allowing the cell into resonance with a laser that is fixed onto a peak of an absorption line of an analyte of interest. To this end, a first actuator 40 can be mounted external to the member lumen and configured to apply a force to a location on the external surface of the optical cell apparatus 20 sufficient to elastically deform at least a portion of the optical cell apparatus such that a longitudinal distance between the first optical element 34 and the second optical element 36 is responsively altered. In one example, the first actuator 40 can be implemented as a piezoelectric transducer.

The actuator 40 can be positioned to apply a force that stretches the tubular body 22, increasing the distance between the optical elements 34 and 36. The displacement of the optical elements, $\Delta L$, can be calculated from the applied force, F, Young's modulus, E, for the material that the tubular body 22 is constructed from, and the cross sectional area of the tubular body, A, as:

$$\Delta L = \frac{L_0 F}{AE} \qquad \text{Eq. 1}$$

where $L_0$ is an original length of the tubular body.

Since the length, area, and material properties of the material are known and constant, the distance between the optical elements 34 and 36 can be controlled by adjusting the force applied by the actuator. It has been determined that the distance can be changed by several wavelengths of the associated light source using commercial, high-force actuators.

It will be appreciated that the system 10 can include additional actuators, for example, mounted in series with the first actuator in an actuator stack such that they all apply for to a same location on the external surface of the optical cell assembly 20. In one implementation, the first actuator 40 is affixed to the first end member 30 and configured to apply a force to the second end member 32 in response to a command from a system control (not shown). To facilitate the application of the force across the distance between the two end members 30 and 32, a rod 42 can be affixed to the first actuator 40 and extend longitudinally between the first actuator and the second end member to transmit force between the first actuator and the second end member. For example, the rod 42 can be implemented as a one inch metallic rod (e.g., stainless steel or Invar) affixed to the actuator 40 with a sapphire ball to minimize any torque applied to the actuator during assembly. It will be appreciated that other sizes and materials can be used for the rod 42, but a rigid material is preferable as compression of the rod by the force generated by the actuator 40 will increase the required displacement of the actuators to deform the optical cell apparatus 20 by a desired amount.

Figure 2:
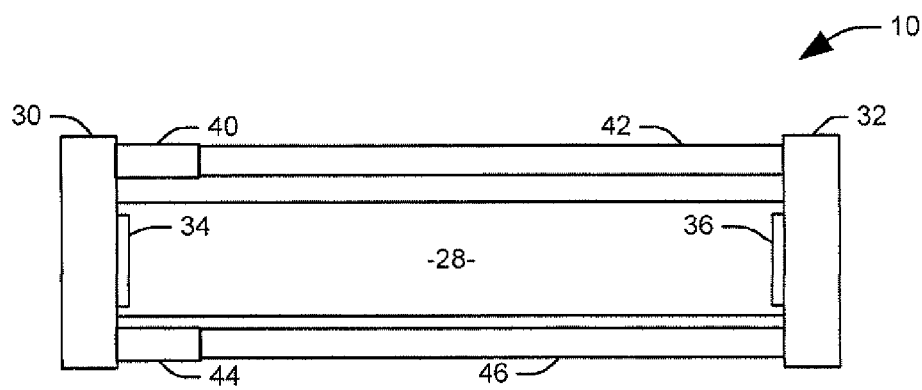
FIG. 2 illustrates a cross-sectional view along a longitudinal axis of one implementation of an adjustable cell assembly in accordance with an aspect of the present invention.
Figure 3:
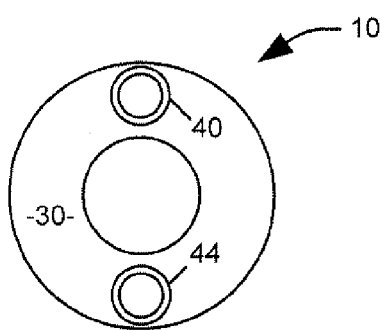
FIG. 3 provides a cross-sectional view along a lateral axis of the assembly of FIG. 2.

FIGS. 2 and 3 illustrate one implementation of an adjustable cell assembly in accordance with an aspect of the present invention. Elements common with FIG. 1 share a common numbering. FIG. 2 provides a cross-sectional view along a longitudinal axis of the assembly 10. FIG. 3 provides a cross-sectional view along a lateral axis of the assembly 10 near the first end member 30, and illustrates the arrangement of the first actuator 40 and a second actuator 44. Each of the first and second end members 30 and 32 comprises vacuum flanges configured to provide a substantially airtight seal with the tubular body 22. The flanges 30 and 32 extend laterally beyond a cross-section of the tubular body 22.

In the illustrated implementation, each of the first and second actuators 40 and 44 comprise a piezoelectric transducer affixed to the first end member 30 and configured to apply a force to the second end member 32 at respective first and second locations. A second rod 46 is affixed to the second actuator 44 and extends longitudinally between the second actuator and the second end member 32 to transmit force between the second actuator 44 and the second end member. The addition of the second actuator 44 provides a number of advantages, including sharing the force necessary to deform the cell body between multiple assemblies, reducing the necessary capacity of each actuator and, assuming the actuators are placed symmetrically around the longitudinal axis, the additional actuator can reduce the likelihood of warping of the cell that would move the optical axis of the cell as the cavity length is scanned. Finally, where multiple actuators are used, they can be configured to provide different levels of force, such that the cell body is unevenly deformed and a relative orientation of the optical elements 34 and 36 is altered.

Figure 4:
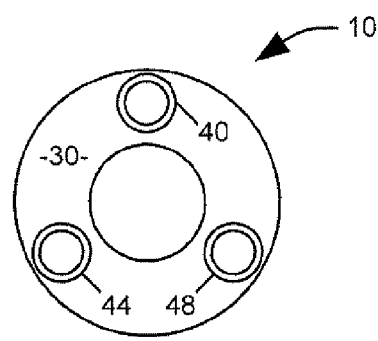
FIG. 4 provides a cross-sectional view along a lateral axis of another implementation of an adjustable cell assembly in accordance with an aspect of the present invention.

FIG. 4 illustrates another implementation of an adjustable cell assembly in accordance with an aspect of the present invention, in which three transducers are used in a symmetrical arrangement as a cross-sectional view along a lateral axis of the assembly 10 near the first end member 30, and illustrates the arrangement of the first, second, and third actuators 40, 44, and 48. By using more actuators, it becomes possible to compensate for any misalignment of the cell caused by uneven expansion of the cell body. Further, it will be appreciated that as more actuators are used, the force needed from each individual actuator is decreased, and the relative orientation of the mirrors 34 and 36 can be controlled with more precision. In general, the assembly can use any practical number, n, of actuators to apply a force to the optical cell apparatus, with each of the plurality of actuators applying a force in a different location on the external surface of the optical cell assembly such that the locations, taken collectively, have n-fold rotational symmetry around an axis of the cylinder defined by the tubular body 22.

Figure 5:
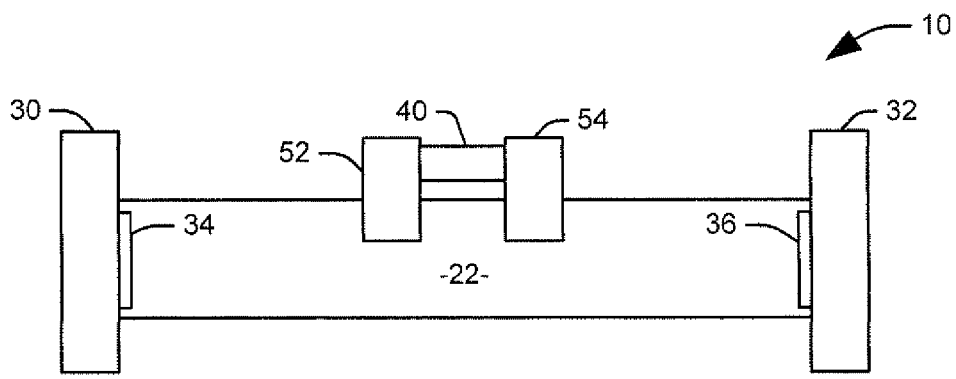
FIG. 5 illustrates a cross-sectional view along a longitudinal axis of yet another implementation of an adjustable cell assembly in accordance with an aspect of the present invention.

FIG. 5 illustrates yet another implementation of an adjustable cell assembly in accordance with an aspect of the present invention as a cross-sectional view along a longitudinal axis, with elements common to FIG. 1 sharing a common numbering. In FIG. 5, one or more intermediate members 52 and 54 are rigidly affixed to an exterior surface of the tubular body at a point between the first end member 30 and the second end member 32. For example, a given intermediate member 52 and 54 can include a flange that is rigidly attached to the cell body, either permanently, via welding, adhesive, or a similar joining process, or temporarily, with a clamp or similar assembly. By temporarily affixing the intermediate member to the cell body, the position can later be changed to account for the use of excitation sources of different wavelengths.

In the illustrated implementation, two intermediate members 52 and 54 are used with the actuator 40 mounted on one intermediate member (e.g., 52) and configured to exert a force on the second intermediate member (e.g., 54). It will be appreciated, however, the actuator 40 could be situated between one of the end members 30 and 32 and a single intermediate member 52, to apply a force from one of an end member 30 and 32 to the intermediate member 52 or from the intermediate member to the end member. It will further be appreciated that actuators can be connected in series, for example, with a first actuator applying a force from an end member (e.g., 30) to a first intermediate member (e.g., 52), a second actuator applying a force from the first intermediate member to a second intermediate member (e.g., 54), and a third actuator applying a force from the second intermediate member to a second end member (e.g., 32). It will be further appreciated that the intermediate members, while illustrated as encompassing only a portion of the arc of the longitudinal cross-section of the tubular body 22, can encompass the entire arc of the body. Accordingly, multiple actuators (not shown) can be used in parallel on one or more of the intermediate members 52 and 54.

The use of the intermediate members 52 and 54 can eliminate or reduce the necessary length of the rods to transfer the force between the end members 30 and 32 in FIG. 2. This reduces the distance over which the force acts on the cell body, thereby increasing the force the PZT's must generate to obtain the same displacement. However, the required extension of the PZT elements is reduced, as the rods used to transfer the force in the assembly of FIGS. 2 and 3 will undergo some compression when the PZT's are stretched.

Figure 6:
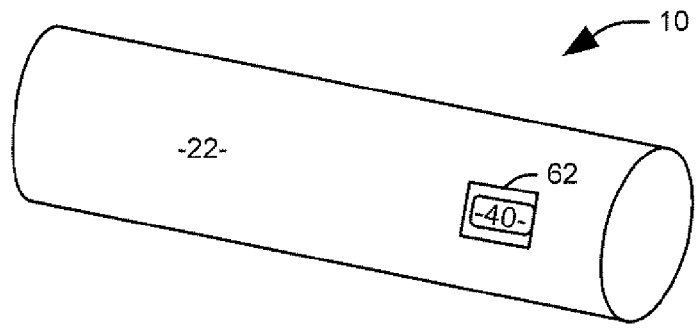
FIG. 6 illustrates still another implementation of an adjustable cell assembly in accordance with an aspect of the present invention.

FIG. 6 illustrates still another implementation of an adjustable cell assembly in accordance with an aspect of the present invention, with elements common to FIG. 1 sharing a common numbering. In the illustrated implementation, a cavity 62 is provided on an outer surface of the tubular body 22, and the first actuator 40 is mounted at least partially within the cavity. For example, the actuator 40 can be press fitted into a notch machined into the tubular body 22. Only one actuator is shown for clarity, but it will be appreciated that multiple cavities can be provided around the circumference of the tubular body. The length of the cavity 62 can be matched to the length of each actuator via precision machining. Alternatively, shims can be used to achieve a tight mating of the actuator 40 with the walls of the cavity 62. In one implementation, the cavity 62 is shaped to allow a tool to reach the side of the actuator 40 closest to the center of the cell to allow removal of the actuators.

It will be appreciated that while the assemblies herein are shown as linear, two element cavities for ease of description, the assemblies and methods herein, particularly the cavity mounted actuator of FIG. 6, are not limited to such an arrangement. To provide a simple example, an assembly can include two tubular members meeting at a corner in an L-shaped arrangement, with a third optical element positioned to allow light to pass freely between the two tubular members. Multiple actuators can be used to elastically deform the two tubular members to adjust the intraelement distances and relative orientations of the first, second, and third optical elements. Other configurations will be apparent to one of skill in the art in light of the systems and methods presented herein.

The systems illustrated in FIGS. 1-6 provide a number of advantages when used in a ring-down spectroscopy system. For example, the cavity length can be scanned into resonance with an associated excitation laser, which is needed to obtain significant cavity transmission to observe the cavity decay. By varying the cavity length instead of the frequency of the excitation laser, the sensitivity of the system is increased by a modest amount, and more importantly, variation of the absorption cross section at the detection wavelength can be minimized. Since the calculation of sample concentration from the observed change in cavity decay rate requires dividing by the absorption cross-section, this avoids a source of uncertainty in this calculation and thus increases the accuracy of the concentration measurement.

By using the adjustable cavity described previously, scanning the laser around the cavity resonance can be kept to a minimum, such that the cavity is almost continually excited. Since the short-term linewidth of many lasers widely used in cavity-enhanced spectroscopy are a small fraction of the absorption linewidth, this is a large effect and can improve the possible detection rate by as much as two orders of magnitude. Also, working at and immediately around the peak of the absorption line minimizes the effect of error in the determination of the laser wavelength and of the spectral width of the laser. It is also worth noting that the adjustable cavity obviates any need for monitoring the cavity and calculating a frequency offset from a peak of the absorption line of the analyte. In samples that have a frequency dependent background absorption, the correction for frequency offset depends upon the precise frequency dependence of that background, and thus it would be better to not have to make that correction.

Finally, some versions of cavity enhanced absorption spectroscopy, particularly a method known as Noise-Immune Cavity-Enhanced Optical Heterodyne Molecular Spectrometry (NICE-OHMS) requires a tight locking of the laser onto the cavity resonance (with residual jitter of ~1 KHz or less) and is thus incompatible with repetitively scanning the laser over the absorption line. The adjustable cavity described herein is suitable for use with such methods.

The addition of multiple actuators also allows for the tilting of one mirror relative to the other, which moves the optic axis of the cavity. This can be used to fine tune the relative alignment of the input laser and cavity, which is useful for optimizing the coupling of the light into the lowest order transverse mode ($TEM_{00}$ mode) of the cavity and for avoiding localized spots of the mirrors that have increased loss due to localized defects in the mirror coatings. Further, by rigidly affixing the mirrors to a surface in the cavity, the system can maintain critical optical alignment when subjected to high levels of vibration or acceleration as is likely to occur in shipping or in many environments where one would to use cavity enhanced spectroscopy.

Figure 7:
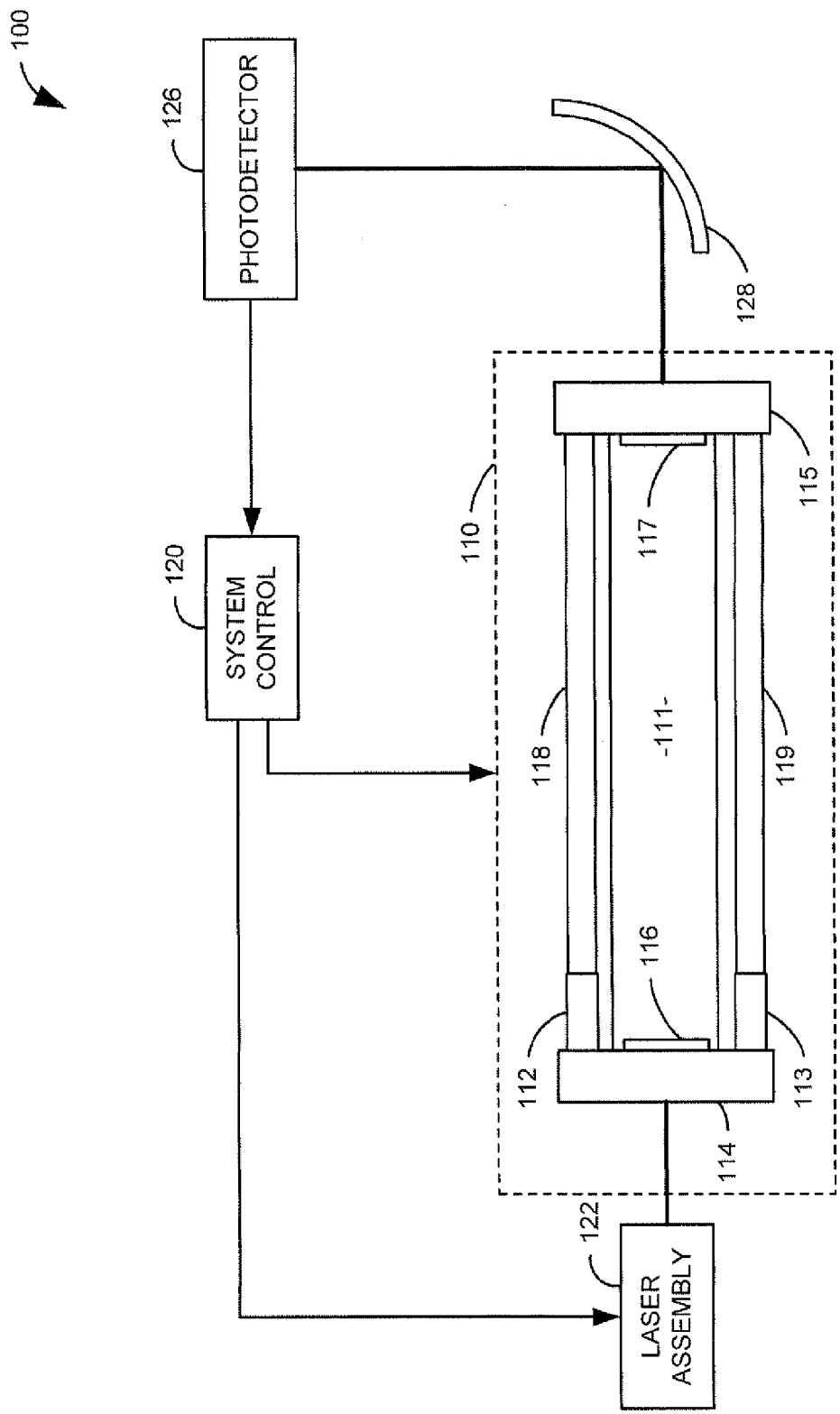
FIG. 7 illustrates a cavity ring-down spectroscopy (CRDS) system utilizing one example of an adjustable length cell in accordance with an aspect of the present invention.

FIG. 7 illustrates a cavity ring-down spectroscopy (CRDS) system 100 utilizing one example of an adjustable length cell in accordance with an aspect of the present invention. Detection of trace species continues to be an important application of optical spectroscopic techniques. CRDS is used for the detection of those species in recent decades because of its long path-length and high sensitivity. Among its advantages is an immunity to the fluctuation of the laser intensity, because CRDS measures the decay rate of the laser power in the cavity. Compared with pulsed-laser CRDS, continuous-wave (cw) CRDS provides narrow bandwidth, which provides high resolution, and stable excitation of only the $TEM_{00}$ modes of the cavity, which is only possible when the excitation laser has a bandwidth much narrower than the free spectral range (FSR) of the cavity, leads to more stable cavity decay rates and thus higher sensitivity of the method. In the IR region, particularly at low pressure, the width of individual rovibrational transitions is comparable to the FSR of cavities of convenient length, and then cw excitation of the cavity is important for the accuracy of the experimentally determined spectrum and the molecular concentrations deduced from it.

When using a spectrally narrow laser, with a linewidth, □□$_L$, less than the FSR of the cavity, one or both of the cavity and the laser is tuned into resonance to allow efficient cavity excitation of one $TEM_{00}$ mode of the cavity. This is can be done by sweeping either the cavity length or the laser frequency. A scan amplitude of the laser of at least one FSR, or of the cavity length of at least □/2, where □ is the wavelength corresponding to the laser frequency, will insure that at least one $TEM_{00}$ mode will come into resonance with the laser on each sweep.

For diode lasers, and many others single mode lasers as well, it is possible to electronically sweep the laser a few hundred MHz, which is typically required to ensure resonance. The disadvantage of this is that, without additional measurement, the optical frequency at which the sample absorption is measured is uncertain by the laser scan amplitude and thus at least one FSR of the cavity. It is possible to measure the laser scan ramp voltage when the cavity ring-down event is initiated by sufficient cavity transmission, and thereby make a correction for the laser frequency modulation, but this often introduces unacceptable error. One cause of this error is phase shifts in the transducer that produces the laser frequency modulation (FM). So, to provide very precise measurements, the laser frequency of the described system 100 is locked, for example, to an absorption line or optical comb tooth, either avoiding frequency modulation entirely or least avoiding the need for frequency modulation used to ramp around the cavity mode.

In the illustrated system, at least one of the mirrors that make up the CRDS cavity is moved by one or more piezoelectric transducer actuators, allowing for electronic control of the mirror position. This has the advantage that each cavity decay occurs with light inside the cavity initially within the bandwidth of the laser. As the cavity scans, the Doppler shift of the light off of the moving mirror will keep the intracavity light in resonance with the scanning mode. For experiments with Doppler broadened lines or broader, this shift in intracavity frequency is negligible. To allow the maintenance of vacuum integrity of the cell while having a moving mirror, a stainless steel cell is utilized with transducers mounted to exterior to elastically deform the cell body and adjust the mirror position, such as the systems described in FIGS. 1-6. By maintaining the actuators external to the cavity, it is possible to avoid exposing the actuator to the gas sample, with the associated risk of contamination, chemical damage to the actuator, or electrical breakdown, which is particularly common when working in the desired pressure range where pressure broadening about matches Doppler broadening, which is desired to simultaneously maximize signal to noise and effective spectral resolution. The use of a rigid steel cell with the mirrors mounted directly thereon reduces the likelihood of misalignment when the cell is subjected to acceleration or significant vibration.

The system 100 includes a stainless steel cell 110 that forms the optical cavity 111. The stainless steel cell 102 has a length of about 40 centimeters which gives an FSR of three hundred eighty megahertz. The outer diameter is 2.9 centimeters. The ending vacuum flanges have an outer diameter of 7.5 centimeters. Two preloaded piezoelectric transducers (PZT) 112 and 113, having a length of 6.5 centimeters are mounted on a first end flange of the stainless steel cell 110 perpendicular to the end flanges 114 and 115 and are used to sweep the length of the cavity 111 to adjust a distance between first and second mirrors 116 and 117. Two stainless steel rods 118 and 119, with a diameter of 1.8 centimeter and a length of 33 centimeters, are attached to the second end flange 115 of the cell by ¼-20 threaded rods to transfer force. In order to minimize compression of the threaded rods, C-shaped spacers (not shown), with a thickness selected so they would produce a snug fit between the end of the rods 118 and 119 and the second end flange 115, are press fit after the rods and PZTs 112 and 113 were mounted. In order to minimize torque on the PZTs 112 and 113 when tightening the rods 118 and 119, a sapphire ball (not shown) is used between them.

The PZTs 112 and 113 are selected to have a maximum open-loop travel distance of thirty micrometers, with a resolution of three-tenths of a nanometer, when a voltage of up to one hundred volts is applied from the system control 120. In the exemplary system 100, the applied voltage was swept between around one and seventeen volts, sufficient to generate a PZT extension of 4.8 micrometers if no resistance were present. The observed travel distance of the mirrors 116-117 was a little larger than 1 FSR (~0.88 micrometers). During the sweep, the PZTs were driven by a twenty hertz triangular wave, generated by a function generator associated with the system control 120 and amplified by a piezo driver.

The displacement of the mirrors 116-117 produced by the force against the end flanges 114 and 115 is given Eq. 1, above. Assuming a distance of 0.4 meter for the length, L, between the end flanges, a cross-sectional area of the cavity body, A, of fifteen cubic centimeters, and a Young's modulus, E, for stainless steel of two hundred seven gigapascals, a force of seven hundred seventy-five newtons is required for each micrometer of displacement. In the illustrated implementation, the PZT actuators 112 and 113 are able to apply three kilonewtons of force, and a corresponding displacement of thirty micrometers, well more than what is needed to sweep the cavity by the required half wavelength even at relatively long infrared wavelengths. Two symmetrically placed PZT actuators 112 and 113 are used to avoid any potential warping of the cell that would move the optical axis of the cell as the cavity length is scanned. It will be noted that the stainless steel rods 118 and 119 used to transmit the force between the ends of the cell will themselves compress while the central cell body expands. If each rod 118 and 119 is stainless steel, has an area of A', and a length of L', each PZT 112 and 113 will expand by a factor of $$\left(1 + \frac{L'A}{2LA'}\right)$$

times the increase in the distance between the mirrors. This factor is around 3.3 for the illustrated cell 102.

In the illustrated cell 102, the input mirror 116 of the cavity is flat and the output mirror 117 has a radius of curvature of one meter. Both mirrors have the back side wedged by 0.55° to prevent laser feedback into the cavity, which could modify the cavity decay rate. A stainless steel ball bearing race (not shown) is positioned between each mirror 116 and 117 and the cell surface against which the mirror is pressed. A stainless steel washer and a stainless steel restraining nut are sequentially used to hold the mirrors against their respective bearing races. The restraining nut on each mirror 116 and 117 is adjusted to optimize the ring-down time constant of the cell 102. By affixing the mirrors 116 and 117 rigidly against steps machined in the stainless steel tube from which cavity is formed, the alignment of the mirrors can be maintained even during acceleration or vibration of the assembly.

The system 100 further includes at least one laser assembly 122 configured to provide transmit a coherent light beam to the cell 110 to excite the optical cavity 111. In one implementation, the laser assembly 122 includes a distribution feedback laser that produces infrared light having a wavelength on the order of around 1650 nanometers. The laser assembly 122 is driven by an ultralow noise current source and the laser temperature is stabilized by using temperature controllers, each associated with the system control 120. For example, the system control 120 can comprise a general purpose processor running software to provide a signal to a 16-bit or 12-bit A/D board to determine the set voltage of the temperature controller, as well as appropriate software for controlling each of a function generator for driving the actuators 112 and 113, and collecting data from an associated photodetector 126. By changing the laser temperature, the laser wavelength/wavenumber can be tuned.

The light leaving the back side of the cavity 111 is focused by using an off-axis parabolic mirror 128 and provided to the photodetector 126. For example, the photodetector 126 can include an InGaAs detector/amplifier that converts received light of the appropriate wavelength into an electrical signal and amplifies it. A pulse/delay generator associated with the system control 120 is used to turn off a semiconductor optical amplifier associated with the laser assembly 122 when the laser intensity on the detector exceeded a preset threshold. The system control 120 fits each ringdown decay transient to a single-exponential decay using a nonlinear fitting algorithm with equal weights of the points. The resulting cavity decay rate is the sum of the loss rate due to the mirrors, $(1-R^2) \times FSR$, where R is the power reflectivity of the mirrors, and the loss due to sample extinction, $c \times \alpha(v)$, where c is the speed of light and $\alpha(v)$ is the extinction coefficient of the gas between the mirrors.

Figure 8:
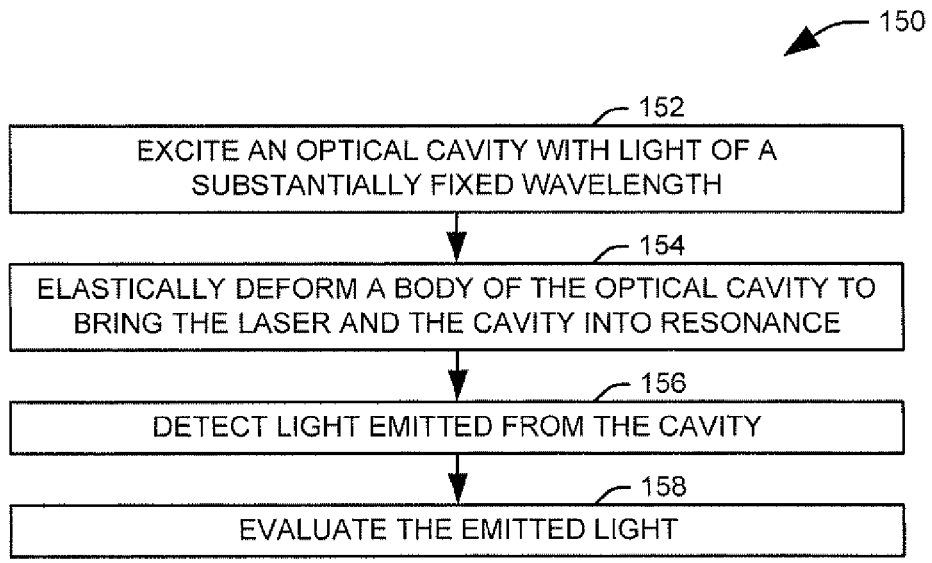
FIG. 8 illustrates a method for determining the concentration of an analyte in accordance with an aspect of the present invention.

In view of the foregoing structural and functional features described above, methodologies in accordance with various aspects of the present invention will be better appreciated with reference to FIG. 8. While, for purposes of simplicity of explanation, the methodology of FIG. 8 is shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect the present invention.

FIG. 8 illustrates a method 150 for determining the concentration of an analyte in accordance with an aspect of the present invention. At 152, an optical cavity, comprising a rigid body and first and second optical elements affixed to the rigid body, is excited with a laser producing light of a substantially fixed wavelength. At 154, the rigid body is elastically deformed in at least a first location to bring the laser and the cavity into resonance. For example, the rigid body can include one or more actuators configured to apply force to associated locations on the rigid body to stretch the body, increasing a distance between the first and second mirrors. Where multiple actuators are used, the rigid body can be deformed unevenly in multiple locations to change a relative orientation of the first and second optical elements. In one implementation, each actuator is selected to apply sufficient force to stretch the rigid body by at least one-half of the substantially fixed wavelength. At 156, light emitted from the cavity is detected. At 158, the detected light is evaluated to determine a concentration of the analyte.

From the above description of the invention, those skilled in the art will perceive improvements, changes, and modifications. Such improvements, changes, and modifications within the skill of the art are intended to be covered by the appended claims.

Having described the invention, I claim:

1. An assembly comprising:
an optical cell apparatus comprising:
a hollow tubular body comprising a wall of the optical cell apparatus, the tubular body having longitudinally spaced first and second body ends and surrounding a longitudinal axis of the optical cell to define a member lumen therethrough;
a first end member that is substantially rigid and attached to the first body end to define a first optical cell end;
a first optical element, located within the member lumen and fixedly attached to the first end member;
a second end member that is substantially rigid and attached to the second body end to define a second optical cell end; and
a second optical element, located within the optical cell and fixedly attached to the second end member; and
a first actuator mounted external to the member lumen and coupled to the first and second end members externally to the member lumen, the first actuator configured to apply a force to displace the first end member relative to the second end member in a direction substantially parallel to the longitudinal axis, the displacement sufficient to elastically deform the hollow tubular body of the optical cell apparatus such that a longitudinal distance between the first optical element and the second optical element is responsively altered.

2. The assembly of claim 1, wherein the first actuator is configured to apply a force to the optical cell apparatus in a first location, the assembly further comprising a second actuator mounted external to the member lumen and configured to apply a force to the optical cell apparatus in a second location, different from the first location, such that a relative orientation of the first optical element and the second optical element can be selectively altered.

3. The assembly of claim 2, wherein the member lumen is a cylinder and the first and second actuators comprise first and second actuators of a plurality of actuators, each of the plurality of actuators being mounted external to the member lumen and being configured to apply a force to the optical cell apparatus in an associated location, the associated locations of the plurality of actuators collectively having n-fold rotational symmetry around an axis of the cylinder defined by the tubular member, where n is an integer greater than one.

4. The assembly of claim 1, wherein each of the first end member and the second end member extend laterally beyond a cross-section of the tubular member taken perpendicular to the longitudinal axis, the first actuator being fixedly attached to a portion of the first end member located laterally outside the member lumen and being configured to apply a force to the second end member to increase the longitudinal distance between the first optical element and the second optical element.

5. The assembly of claim 1 further comprising a rigid rod affixed to the first actuator and extending longitudinally between the first actuator and the second end member to transmit force between the first actuator and the second end member.

6. The assembly of claim 1, the optical cell apparatus further comprising an intermediate member rigidly affixed to an exterior surface of the tubular body at a point between the first end member and the second end member.

7. The assembly of claim 6, wherein the first actuator is affixed to a selected one of the first end member and the intermediate member and is configured to exert a force upon the other one of the first end member and the intermediate member.

8. The assembly of claim 6, wherein the intermediate member is a first intermediate member and the optical cell apparatus further comprises a second intermediate member rigidly attached to an exterior surface of the tubular body between the first end member and the second end member, the first actuator being mounted on the first intermediate member and configured to exert a force on the second intermediate member.

9. The assembly of claim 1, wherein a cavity is provided on an outer surface of the tubular body and the first actuator is mounted at least partially within the cavity.

10. The assembly of claim 1, wherein the first actuator is a piezoelectric transducer.

11. The assembly of claim 1, wherein the first and second optical elements are first and second mirrors.

12. The assembly of claim 1, wherein the tubular body is formed from one of stainless steel and Invar.

13. The assembly of claim 1, further comprising a second actuator arranged in series with the first actuator such that each of the first actuator and the second actuator apply a force on a same location of the external surface.

14. A cavity ring-down spectroscopy apparatus comprising:
the assembly of claim 1;
a laser assembly configured to provide light to the optical cell apparatus;
a system control configured to control the first actuator such that the distance between the first optical element and the second optical element can be dynamically selected within a predetermined range; and
a detector configured to detect light emitted from the optical cell apparatus and provide an electrical signal representing the emitted light to the system control.

15. A method for determining the concentration of an analyte, comprising:
exciting an optical cavity, comprising a rigid tubular body and first and second optical elements affixed to the rigid tubular body, with a laser producing light of a substantially fixed wavelength;
using an actuator coupled to the rigid tubular body elastically deforming the rigid tubular body in a longitudinal direction to bring the laser and the cavity into resonance;
detecting light emitted from the cavity; and
evaluating the detected light to determine the concentration of the analyte.

16. The method of claim 15, further comprising elastically deforming the rigid body in at least first and second locations to change a relative orientation of the first and second optical elements.

17. The method of claim 15, wherein elastically deforming the rigid body comprises stretching the rigid body by at least one-half of the substantially fixed wavelength.

* * * * *